United States Patent [19]

Bauman

[11] Patent Number: 4,573,451

[45] Date of Patent: Mar. 4, 1986

[54] LARYNGOSCOPE BLADE WITH A BENDABLE TIP

[76] Inventor: Jack Bauman, 1677 San Onofre Dr., Pacific Palisades, Calif. 90272

[21] Appl. No.: 669,475

[22] Filed: Nov. 8, 1984

[51] Int. Cl.⁴ .............................................. A61B 1/26
[52] U.S. Cl. .................................................. 128/11
[58] Field of Search ........................... 128/11, 10, 4, 6

[56] References Cited

U.S. PATENT DOCUMENTS

| | | | |
|---|---|---|---|
| 3,426,749 | 2/1969 | Jephcott | 128/11 |
| 3,598,113 | 8/1971 | Moore | 128/11 |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 4,037,588 | 7/1977 | Heckele | 128/11 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/11 |
| 4,314,551 | 2/1982 | Kadell | 128/11 |
| 4,320,745 | 3/1982 | Bhitiyakul et al. | 128/11 |
| 4,337,761 | 7/1982 | Upsher | 128/11 |
| 4,384,570 | 5/1983 | Roberts | 128/4 |

*Primary Examiner*—William H. Grieb
*Attorney, Agent, or Firm*—Fulwider, Patton, Rieber, Lee & Utecht

[57] ABSTRACT

The invention is directed to a laryngoscope blade which has a tip at the distal end thereof which is capable of being bent or flexed in the direction of the handle of the laryngoscope. Operable means are provided, preferably at the proximal end of the blade, to bend or flex the tip. When the blade is inserted into a patient's throat so that the bendable tip is located at the base of the patient's epiglottis, the operable means of the bendable tip can be actuated so the tip will bend and thereby further lift the patient's epiglottis in order to expose the patient's larynx. The laryngoscope blade is particularly suitable to the few patients in which the usual laryngoscopic procedures do not adequately expose the patient's larynx.

13 Claims, 6 Drawing Figures

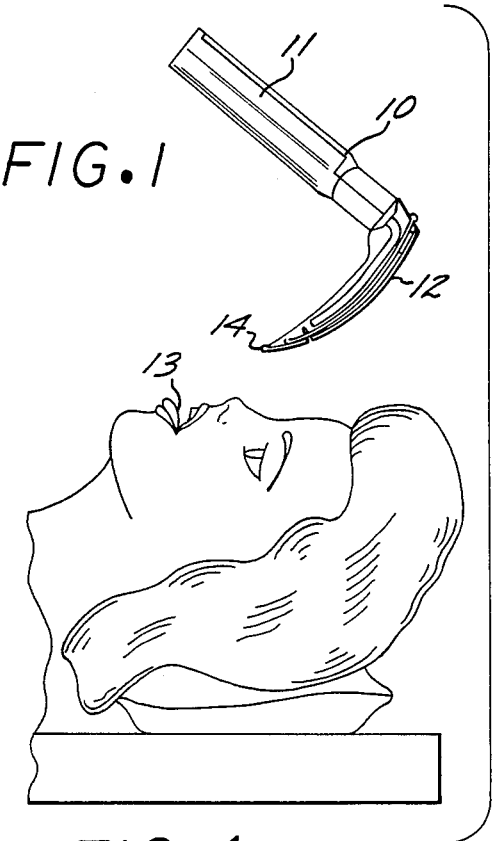
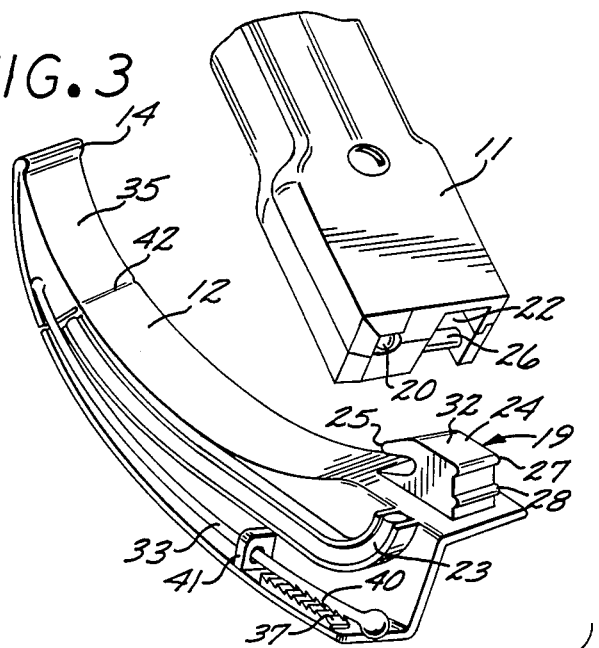
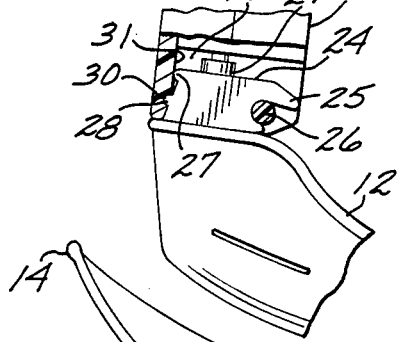
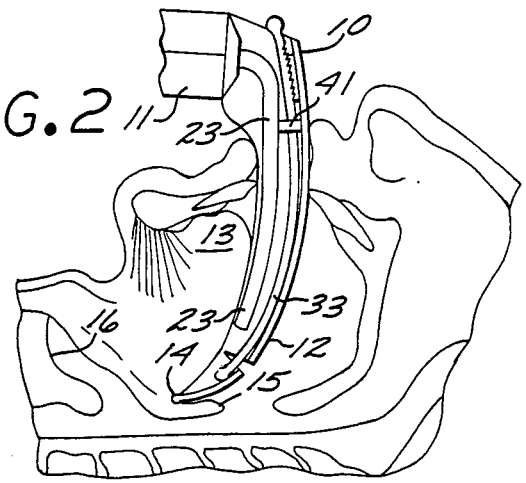
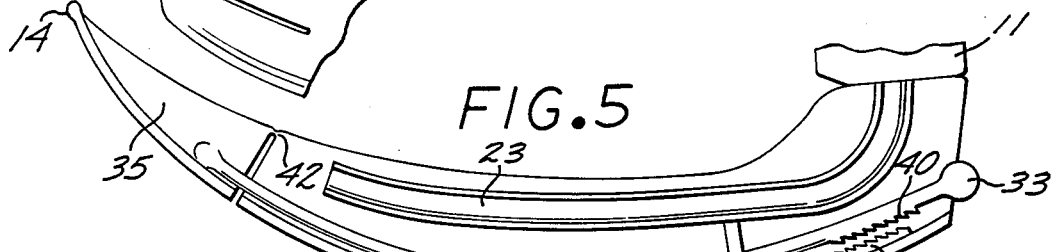
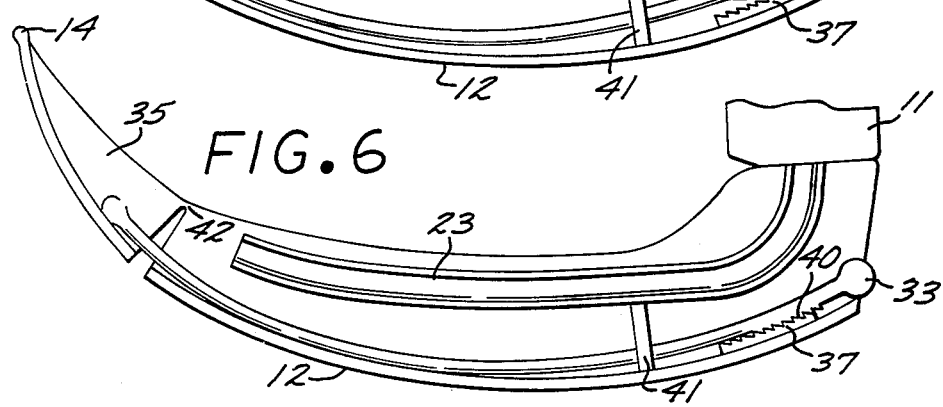

LARYNGOSCOPE BLADE WITH A BENDABLE TIP

BACKGROUND OF THE INVENTION

This invention generally relates to examining or viewing devices such as laryngoscopes, and particularly to an improved blade therefore having a bendable tip.

Laryngoscopes generally comprise a blade and a cooperating, detachable handle which are connected together into an L-shaped configuration. When using the device to view the larynx, the surface on the blade adjacent the handle is used to press against the tongue and mandible of a patient in a supine position in order to prevent the patient's tongue from obstructing the view during the visual examination. While the instrument is useful in examining the larynx, the primary function of the laryngoscope is to expose the larynx in order to facilitate the insertion of an endotracheal tube into the trachea of the lungs to administer gases.

During the use of the instrument, when pressed against the patient's tongue and mandible, the tip or distal end of the blade is usually positioned at the junction between the base of the tongue and the base of the epiglottis which is thin, leaf shaped lamella in front of the superior opening of the larynx. With most patients, the epiglottis will be lifted sufficiently to expose the larynx by rotating the instrument anteriorly (i.e., longitudinally). Usually the patient's head is tilted backwardly to facilitate the examination.

With a small fraction of patients, the epiglottis will not be lifted sufficiently to expose the larynx in the usual laryngoscopic procedures. Unfortunately, the small percentage of patients having the anatomical structure which makes the examination of the larynx difficult cannot be determined by visually examining the epiglottis before inserting the laryngoscope. Usually, it is not until the anesthesiologist tries to expose the larynx to administer anesthetic gases, that the difficulty is encountered. The anesthesiologist must then replace the blade being used with a longer and straighter blade which is used to contact the upper edge of the epiglottis and push the epiglottis anteriorly to expose the larynx. However, the view of the larynx is not very complete in this instance and damage is frequently done to the tissue trying to push the epiglottis far enough out of the way to effectively expose the larynx.

The need for a larynogoscope which will readily expose the larynx in those patients in which the normal laryngoscopic procedures do not work has been long felt. The present invention satisfies these needs.

SUMMARY OF THE INVENTION

The present invention is directed to an improved blade for an examining device and particularly to a laryngoscope blade which will expose the larynx of those patients in which the normal laryngoscopic procedures are not effective.

In accordance with the present invention, the laryngoscope blade is provided with a bendable or flexible tip at the distal end thereof so that, when the blade is inserted into the patient's throat and the tip of the blade is located at the base of the tongue in front of the epiglottis, the tip or distal end of the blade can be longitudinally pivoted with respect to the main body of the blade to a more anterior position to further move the epiglottis and to thereby expose the larynx in those cases where the normal laryngoscopic procedures are not effective.

Tip movement need not be more than about 2.5 cm and in most instances one cm tip movement is enough to expose the larynx.

In a preferred embodiment, means to bend or rotate the distal end of the blade are provided which are operable at the proximal end of the blade so the tip of the blade can be bent or flexed after it has been inserted into the patient's throat.

In one embodiment the means to bend or rotate the tip of the blade is an elongated rod positioned along one side of the blade and attached to the tip of the blade, so that when the rod is pushed from the proximal end thereof, the tip of the blade is rotated.

If the blade is made of plastic or similar materials, the connecting portion between the main body of the blade and the flexible tip at the distal end of the blade is thinned so that the tip will readily rotate or bend about this line of weakness. If made of stronger material such as metal, the tip of the blade can be hinged at this point to allow for the desired rotation.

These and other advantages will become more apparent from the following detailed description and the exemplary drawings.

BRIEF DESCRIPTION OF THE DRAWINGS

FIG. 1 is a side elevational view of a laryngoscope embodying features of the invention prior to being used in a patient;

FIG. 2 is a cross sectional view of a patient with the laryngoscope blade positioned in the patient's throat prior to exposing the patient's larynx;

FIG. 3 is a perspective exploded view of the blade and handle of the laryngoscope of FIG. 1;

FIG. 4 is a partial, side elevational view, partially in section with the blade in the operative position; and FIGS. 5 and 6 are side elevational views of a blade illustrating the operation of the flexible tip thereof.

DETAILED DESCRIPTION OF THE INVENTION

Reference is made to the drawings which illustrate a laryngoscope and particularly a laryngoscope blade embodying features of the present invention. As shown in FIG. 1, the laryngoscope 10, which comprises a handle 11 and a blade 12, is utilized to depress the patient's tongue and mandible 13. In the usual laryngoscopic examination, the distal end 14 of the blade 12 is at the base of the patient's epiglottis 15 as shown in FIG. 2 and when the laryngoscope 10 is pushed against the tongue 13 and rotated to move the patient's tongue 13 out of the line of sight, the tip of the blade 10 pushes on the base of the epiglottis 15 to move the epiglottis 15 out of the line of sight and to thereby expose the patient's larynx 16.

In general, as shown in FIGS. 2-4, the laryngoscope 10 comprises a handle 11, a detachable blade 12, connection means 19 to detachably secure the blade 12 to the handle 11 in a generally L-shaped configuration, a light source 20, a light switch 21 in channel 22 to energize the light source 20 and a light conductor 23 in the blade 12.

The elongated blade 12 is attached by connecting means 19 to the handle 11 in a pivotal fashion. The connecting means 19 is provided with an appendage 24 which is inserted into the open top channel 22 in the upper portion of handle 11 with a pivotal motion so that the front end 25 of the appendage 24 is hooked under the pivot rod 26 provided in the channel 22. Detents 27 or 28 engage a groove 30 in the back surface or wall 31 of the channel 22 to urge the appendage 24 into a more firm engagement with the pivot rod 26 and to thereby fix the blade 12 with respect to the handle 11. When the blade 12 is in operating position as shown in FIG. 4, the surface 32 of the appendage 24 activates light switch 21 to energize the light source 20 by suitable power source such as one or more batteries (not shown) provided in the handle 11. Light emitted by the light source 20 is directed to a light conductor 23 in the blade 12 which transmits the light to the distal end of the blade 12.

The operation of the flexible tip 35 is best shown in FIGS. 5 and 6, when taken in conjunction with the overall views shown in FIGS. 2 and 3. A push rod 33 is positioned along the web of the blade 12 and the distal end 34 thereof is fixed to the flexible tip 35 at a position thereon, so that, as shown in FIG. 6, when the rod 33 is pushed at the proximal end 36 thereof the tip 35 is bent or flexed toward the handle 11. In this manner, the patient's epiglottis 15 can be further lifted so that the patient's larynx 16 can be seen even in the few cases where the normal laryngoscope procedures are not very effective. A ratcheted surface 37 is provided on inner surface 38 of upper flange 39 of blade 12. The proximal end 36 of the push rod 33 is provided within surface 40 similarly ratcheted but with the teeth thereof in the opposite direction of the teeth of the ratcheted surface 37. In this manner, when the rod 33 is pushed to rotate the bendable tip 35 of the blade 12 during use the two ratcheted surfaces 37 and 40 interdentally engage to therby lock the rod 33 into position. With the bendable tip 35 holding the epiglottis 15 out of the line of sight, an endotracheal tube can be easily inserted through the larynx 16. Guide element 41 holds the rod 33 in alignment and adjacent to the blade 12 so the rod does not bow laterally in the locked position. When in the locked position the rod 33 is arched up against the inner surface 38 of the flange 39 so that the teeth of ratcheted surfaces 37 and 40 interdentally fit together and thereby ensure a locked connection.

Other means can be used to rotate the tip 35 of the blade 12. For example, a pulling system could be used to pull the tip 35 of the blade 12 toward the handle 11 in the desired manner. In the latter instance, however, the pulling element is connected to the flexible tip 35 much closer to the distal end of the blade than the previously described embodiment utilizing a pusher rod 33. Other locking means can be utilized in lieu of the ratcheted surfaces to lock the rod 33 into position. For example, the ratcheted surface 40 may be replaced with a pawl like element which interfits the teeth of ratchet surface 37.

In the particular embodiment shown in FIGS. 5 and 6, the blade section 42 is thinned sufficiently to allow the tip 35 to be bent or rotated but is thick enough so that the tip 35 will not break off in use. The plastic blade is generally designed to be disposable, which means the tip 35 will be bent once, so there is little concern regarding fatigue failure in the thinned section 42. When inserted into the patient's throat, the tip will be moved toward the handle by the push rod 33 and then the rod 33 will be locked in position by the action of the ratcheted surfaces. After use, the push rod 33 is unlocked by pushing on the distal end and disengaging the ratcheted surfaces 37 and 40 and the blade 12 is removed from the patient's throat. After use, the blade 12 is detached from the handle and may be discarded.

Improvements and modifications can be made to the invention without departing from the inventive concepts thereof.

I claim:
1. An elongated laryngoscope blade comprising:
   (a) a main body;
   (b) a separate, flexible tip adjacent the distal end of the main body;
   (c) a continuous flange extending along a substantial length of the blade and interconnecting the main body and flexible tip, the portion of the flange between the main body and flexible tip having a pivot means; and
   (d) means to urge the flexible tip about the pivot means.
2. The laryngoscope blade of claim 1 wherein means are provided to lock the tip in a pivoted position.
3. The laryngoscope of claim 2 wherein the lock means are located at the proximal end of the blade.
4. The laryngoscope blade of claim 3 wherein the operable means to pivot the tip is an elongated pusher rod.
5. The laryngoscope blade of claim 4 wherein a ratcheted surface having a plurality of teeth sloped in one direction is provided at the proximal end of the blade and a ratcheted surface is provided on the proximal end of the pusher bar having teeth sloped in a direction opposite to that of the ratcheted surface at the proximal end of the blade so that when the pusher bar is pushed forward to bend the tip of the blade, the proximal end of the rod may be locked by interdentally engaging the ratcheted surface of the rod with a ratcheted surface at the proximal end of the blade.
6. The laryngoscope blade of claim 1 wherein the pivotal means of the continuous flange is a thinned transverse section where the blade tip is to be pivoted.
7. The laryngoscope blade of claim 1 wherein the pivotal means of the continuous flange tip is a hinge where the blade tip is to be pivoted.
8. In a laryngoscope having an elongated blade, a handle and means to detachably secure the elongated blade to the handle, an improved elongated blade comprising
   (a) a main body;
   (b) a separate, flexible tip adjacent the distal end of the main body;
   (c) a continuous flange extending along a substantial length of the blade and interconnecting the main body and flexible tip, the portion of the flange between the main body and flexible tip having a pivot means; and
   (d) means to urge the flexible tip about the pivot means.
9. The laryngoscope of claim 8 wherein means are provided to lock the tip in the bent or flexed position.
10. The laryngoscope of claim 8 wherein the tip of the blade is pivoted by means operable from the proximal end of the blade.
11. The laryngoscope of claim 10 wherein the means to pivot the tip comprises an elongated rod slidably mounted to the side or web of the blade and fixed to the flexible tip.
12. The laryngoscope of claim 11 wherein means are provided at the proximal end of the blade to lock the rod into position after the rod has been pushed forward to pivot the tip of the blade to thereby lock the flexible tip in a fixed pivoted position.
13. The laryngoscope of claim 12 wherein the locking means comprises a ratcheted surface on the proximal end of the blade and a ratcheted surface or a pawl-like element on the proximal end of the rod which interfits the ratcheted surface on the blade.

* * * * *